United States Patent
Fertig et al.

(10) Patent No.: US 7,098,247 B2
(45) Date of Patent: Aug. 29, 2006

(54) ARYLENE-CARBOXYLIC ACID (2-AMINO-PHENYL)-AMIDE DERIVATIVES

(75) Inventors: Georg Fertig, Penzberg (DE); Frank Herting, Penzberg (DE); Matthias Koerner, Antdorf (DE); Manfred Kubbies, Penzberg (DE); Anja Limberg, Munich (DE); Ulrike Reiff, Penzberg (DE); Michael Weidner, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 54 days.

(21) Appl. No.: 10/732,026

(22) Filed: Dec. 10, 2003

(65) Prior Publication Data
US 2004/0138270 A1   Jul. 15, 2004

(30) Foreign Application Priority Data
Dec. 10, 2002  (EP) .................................. 02027579

(51) Int. Cl.
*A61K 31/16*  (2006.01)
(52) U.S. Cl. ..................... 514/616; 615/564; 615/138; 615/155
(58) Field of Classification Search ............... 514/615, 514/616; 564/138, 155
See application file for complete search history.

(56) References Cited

U.S. PATENT DOCUMENTS 3,810,910 A      5/1974   Meyer et al.
5,137,918 A  *   8/1992   Weiershausen et al. ....... 514/616

FOREIGN PATENT DOCUMENTS

DE   2062265     5/1972
EP   0242851    10/1987
EP   0847992     6/1998
FR   2167954     8/1973

OTHER PUBLICATIONS

Lu, Qiang et al 'Zn2+ chelating motif-tethered short-chain fatty acids as novel class of histone deacetylase inhibitors' J. Med. Chem. 2004, 47, 467-474.*
Hassan, H. et al., Indian J. Chem. 39B, 2000, p. 764-768.
Koyama, Y. et al., Blood 96, 2000, p. 1490-1495.
Millot, N. et al., Synthesis 7, 2000, p. 941-948.
Moll, R. et al., Z. Chem. 17, 1977, p. 133-134.
Rastogi, R. and Sharma, S., Indian J. Chem., Sect. B, 21B, 1982, p. 485-487.
Vorbruegghen, H. and Krolikeiewicz, Synthesis 4, 1983, p. 316-319.

* cited by examiner

*Primary Examiner*—Amelia A. Owens
(74) *Attorney, Agent, or Firm*—George W. Johnston; Patricia S. Rocha-Tramaloni; Brian C. Remy

(57) ABSTRACT

The present invention describes compounds of the general formula I

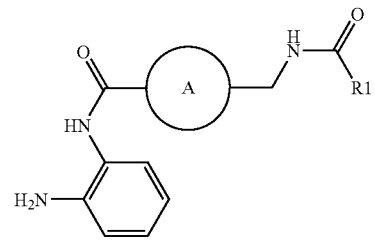

as well as processes for their manufacture, pharmaceutical compositions containing them and methods for using these compounds and pharmaceutical compositions as pharmaceutical agents. The compounds according to this invention show antiproliferative and differentiation-inducing activity, which results in inhibition of tumor cell proliferation, induction of apoptosis and inhibition of invasion.

37 Claims, No Drawings

ARYLENE-CARBOXYLIC ACID (2-AMINO-PHENYL)-AMIDE DERIVATIVES

BACKGROUND OF THE INVENTION

1. Field of the Invention

The present invention relates to novel arylene-carboxylic acid (2-amino-phenyl)-amide derivatives, to a process for their manufacture, medicaments containing them and their manufacture as well as the use of these compounds as pharmaceutically active agents.

2. Description

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490–1495).

EP-A 0 847 992 describes monoacylated o-phenylenediamine derivatives as cell differentiation inducers. The same type of compounds is also the subject of EP-A 0 242 851. The compounds described in these applications are almost exclusively o-phenylene derivatives monoacylated with derivatives of benzoic acid. However, there is still a need to provide compounds with improved properties such as increased tolerability, less toxicity and less side effects.

Monoacylated o-phenylenediamines are known in the art as precursors for the preparation of the corresponding benzimidazoles, such preparation methods are e.g. described in DE-A 2 062 265; FR 2 167 954; Rastogi, R., and Sharma, S., Indian J. Chem., Sect. B, 21B (5) (1982) 485–487; Moll, R., et al., Z. Chem. 17 (1977) 133–134; and Hassan, H., et al., Indian J. Chem. 39B (2000) 764–768.

A further shortcoming of many anti-cancer drugs is a lack of selectivity. They do not sufficiently differentiate between tumor cells and normal cells, and therefore adverse reactions expressed in normal cells have limited their use in therapy. Up to now, no satisfactory drugs have been discovered, and thus an anticancer drug with reduced toxicity, better tolerability and a high therapeutic effect is very much desired. The compounds of the present invention surprisingly show low toxicity, together with a potent anti-proliferative and cell differentiation activity.

SUMMARY OF THE INVENTION

The present invention provides for compounds of the general formula I

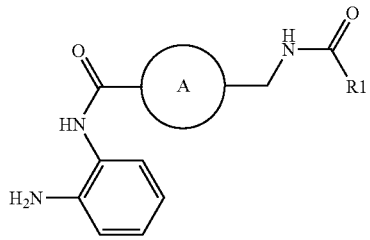

wherein A and $R^1$ defined in detail below.

The present invention also provides for compounds of formula I-A

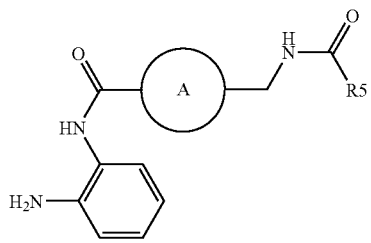

wherein A and R5 are defined in detail below.

The compounds according to this invention are inhibitors of histone deacetylase (HDAC) and therefore show antiproliferative and differentiation-inducing activity, which results in inhibition of tumor cell proliferation, induction of apoptosis and inhibition of invasion.

In accordance with the present invention, there are also provided pharmaceutically acceptable salts and enantiomeric forms of the above-described compounds. Furthermore, the present invention also provides for methods of preparing the above-mentioned compounds, medicaments containing them and the use of the above-mentioned compounds in the control or prevention of illnesses, especially of illnesses and disorders as mentioned above or in the manufacture of corresponding medicaments.

The medicaments provided by the present invention contain one or more compounds according to this invention as active ingredients together with pharmaceutically acceptable adjuvants. The present invention further provides for methods of administering such medicaments for the treatment of cancer by inhibiting tumor cell proliferation through induction of histone acetylation in said tumor cell. Further, the present invention provides for a method for inhibiting tumor cell proliferation, characterized by induction of histone acetylation in a tumor cell, by administering an effective amount of one or more compounds according to the present invention.

DETAILED DESCRIPTION OF THE EMBODIMENTS

As used herein, the term "alkyl" means a straight-chain or branched-chain hydrocarbon group containing from 1 to 14, preferably from 1 to 8, carbon atoms, such as methyl, ethyl, n-propyl, isopropyl, 1-butyl, iso-butyl, sec-butyl, t-butyl, n-pentyl, n-hexyl, n-heptyl as well as their isomers. The alkyl group is optionally substituted once or several times with halogen, hydroxy, cyano, nitro, amino, —NH-alkyl or —N(alkyl)$_2$. Preferably the alkyl group is mono or multiply substituted by fluor or mono substituted by —NH-alkyl or —N(alkyl)$_2$. Examples for fluorinated alkyl groups are perfluormethyl, 2,2,2-trifluorethyl, perfluorethyl. The alkyl group in —N(alkyl)$_2$ substituents is the same or different alkyl group and has the meaning as defined above. Examples for —NH-alkyl or —N(alkyl)$_2$ substituents are methylamino, ethylamino, propylamino, isopropylamino, 1-butylamino, 2-butylamino, t-butylamino, di-methylamino, di-ethylamino, di-propylamino, di-isopropylamino, di-1-butylamino, di-2-butylamino, di-t-butylamino, ethyl-methylamino, ethyl-propylamino.

The term "alkenyl" means an unsaturated alkyl chain as defined above, containing one or two isolated double bonds, preferably one double bond. Examples are 1-propenyl, 2-propenyl, 1-butenyl, 2-butenyl, 1-pentenyl or 1-hexenyl.

The term "alkynyl" means an unsaturated alkyl chain as defined above, containing a triple bond. Examples are 1-propynyl, 2-propynyl, 1-butynyl, 2-butynyl, 1-pentynyl or 1-hexynyl.

The term "optionally substituted" as used herein in combination with alkenyl or alkynyl refers to the substitution of one or several hydrogen atoms at any of the aforementioned groups with halogen, hydroxy, cyano, nitro, amino, oxo, —NHalkyl or —N(alkyl)$_2$.

The term "halogen" means fluorine, chlorine, bromine or iodine.

One embodiment of the invention are compounds of the general formula I

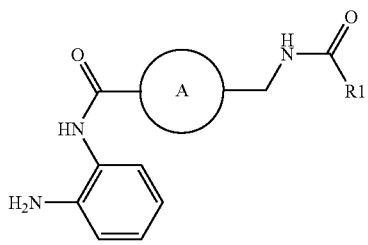

wherein
A represents thiophene-diyl, phenylene or pyridine-diyl;
R$^1$ represents alkyl, alkenyl, alkynyl which are all optionally substituted; or
 —CH$_2$—(O—CH$_2$—CH$_2$—)$_m$O-alkyl;
 —(CH$_2$)$_n$—O-alkyl;
 —(CH$_2$)$_n$—C(O)—NH-alkyl;
 —(CH$_2$)$_n$—NH—C(O)-alkyl;
 —(CH$_2$)$_n$—C(O)alkyl;
 —(CH$_2$)$_n$—C(O)—O-alkyl; or
 —(CH$_2$)$_n$—O—C(O)-alkyl; or
a group —NR$^3$R$^4$, wherein R$^3$ and R$^4$ independently represent hydrogen;
 alkyl, alkenyl or alkynyl which are all optionally substituted; or
 —CH$_2$—(O—CH$_2$—CH$_2$—)$_m$O-alkyl;
 —(CH$_2$)$_n$—(O)-alkyl;
 —(CH$_2$)$_n$—C(O)—NH-alkyl;
 —(CH$_2$)$_n$—NH—C(O)-alkyl;
 —(CH$_2$)$_n$—C(O)alkyl;
 —(CH$_2$)$_n$—C(O)—O-alkyl; or
 —(CH$_2$)$_n$—O—C(O)-alkyl;
n is 1–6;
m is 1–4;

and pharmaceutically acceptable salts thereof.
Another embodiment of the invention are the compounds of formula I, wherein
A represents thiophene-diyl, phenylene or pyridine-diyl;
R$^1$ is a group —NR$^3$R$^4$, wherein R$^3$ is hydrogen and R$^4$ is as defined above;

and pharmaceutically acceptable salts thereof.
Another embodiment of the invention are compounds of formula I, wherein
A represents thiophene-diyl, phenylene or pyridine-diyl;
R$^1$ represents alkyl, alkenyl, alkynyl which are all optionally substituted; or
 —CH$_2$—(O—CH$_2$—CH$_2$—)$_m$O-alkyl;
 —(CH$_2$)$_n$—O-alkyl;
 —(CH$_2$)$_n$—C(O)—NH-alkyl;
 —(CH$_2$)$_n$—NH—C(O)-alkyl;
 —(CH$_2$)$_n$—C(O)alkyl;
 —(CH$_2$)$_n$—C(O)—O-alkyl; or
 —(CH$_2$)$_n$—O—C(O)-alkyl;
n is 1–6;
m is 1–4;

and pharmaceutically acceptable salts thereof.
Yet another embodiment of the invention are compounds of formula I, wherein
A represents thiophen-2,5-diyl;
R$^1$ represents alkenyl;
 —(CH$_2$)$_n$—O-alkyl;
 —(CH$_2$)$_n$—NH—C(O)-alkyl; or
 —(CH$_2$)$_n$—C(O)alkyl;
n is 1–6;

and pharmaceutically acceptable salts thereof.
Such compounds include, for example:
5-[(2-ethoxy-acetylamino)-methyl]-thiophene-2-carboxylic acid (2-amino-phenyl)-amide,
5-(pent-4-enoylamino-methyl)-thiophene-2-carboxylic acid (2-amino-phenyl)-amide,
5-[(2-acetylamino-acetylamino)-methyl]-thiophene-2-carboxylic acid (2-amino-phenyl)-amide,
5-({2-[2-(2-methoxy-ethoxy)-ethoxy]-acetylamino}-methyl)-thiophene-2-carboxylic acid (2-amino-phenyl)-amide,
5-[(4-oxo-pentanoylamino)-methyl]-thiophene-2-carboxylic acid (2-amino-phenyl)-amide.

Yet another embodiment of the invention are compounds of formula I, wherein
A represents thiophen-2,5-diyl;
R$^1$ is a group —NR$^3$R$^4$, wherein
R$^3$ is hydrogen;
R$^4$ is alkenyl;
 alkynyl;
 —(CH$_2$)$_n$—(O)-alkyl;
 —(CH$_2$)$_n$—NH—C(O)-alkyl; or
 —(CH$_2$)$_n$—C(O)—O-alkyl;
n is 1–6;

and pharmaceutically acceptable salts thereof.
Such compounds include, for example:
5-[3-(3-ethoxy-propyl)-ureidomethyl]-thiophene-2-carboxylic acid (2-amino-phenyl)-amide,
5-[(3-prop-2-ynyl-ureido)-methyl]-thiophene-2-carboxylic acid (2-amino-phenyl)-amide, 5-[3-(2-acetylamino-ethyl)-ureidomethyl]-thiophene-2-carboxylic acid (2-amino-phenyl)-amide,
5-[3-(2-methoxy-ethyl)-ureidomethyl]-thiophene-2-carboxylic acid (2-amino-phenyl)-amide,
5-[(3-allyl-ureido)-methyl]-thiophene-2-carboxylic acid (2-amino-phenyl)-amide,
5-[3-(3-butoxy-propyl)-ureidomethyl]-thiophene-2-carboxylic acid (2-amino-phenyl)-amide,
4-{3-[5-(2-amino-phenylcarbamoyl)-thiophen-2-ylmethyl]-ureido}-butyric acid ethyl ester.

Yet another embodiment of the invention are compounds of formula I, wherein
A represents 1,4-phenylene;
$R^1$ represents alkenyl;
—$CH_2$—(O—$CH_2$—$CH_2$—)$_m$O—$CH_3$;
—($CH_2$)$_n$—O-alkyl; or
—($CH_2$)$_n$—NH—C(O)-alkyl;
n is 1–6;
m is 1–4;

and pharmaceutically acceptable salts thereof.
Such compounds include, for example:
N-(2-amino-phenyl)-4-[(2-ethoxy-acetylamino)-methyl]-benzamide,
N-(2-amino-phenyl)-4-(pent-4-enoylamino-methyl)-benzamide,
N-(2-amino-phenyl)-4-({2-[2-(2-methoxy-ethoxy)-ethoxy]-acetylamino}-methyl)-benzamide,
4-[(2-acetylamino-acetylamino)-methyl]-N-(2-amino-phenyl)-benzamide.

Yet another embodiment of the invention are compounds of formula I, wherein
A represents 1,4-phenylene;
$R^1$ is a group —$NR^3R^4$, wherein
$R^3$ is hydrogen;
$R^4$ is alkenyl;
alkynyl;
—($CH_2$)$_n$—(O)-alkyl;
—($CH_2$)$_n$—NH—C(O)-alkyl; or
—($CH_2$)$_n$—C(O)—O-alkyl;
n is 1–6;

and pharmaceutically acceptable salts thereof.
Such compounds include, for example:
4-[3-(2-acetylamino-ethyl)-ureidomethyl]-N-(2-amino-phenyl)-benzamide,
N-(2-amino-phenyl)-4-[3-(2-methoxy-ethyl)-ureidomethyl]-benzamide,
N-(2-amino-phenyl)-4-[3-(3-butoxy-propyl)-ureidomethyl]-benzamide,
N-(2-amino-phenyl)-4-[3-(3-ethoxy-propyl)-ureidomethyl]-benzamide,
4-[(3-allyl-ureido)-methyl]-N-(2-amino-phenyl)-benzamide,
N-(2-amino-phenyl)-4-[3-(3-isopropoxy-propyl)-ureidomethyl]-benzamide,
N-(2-amino-phenyl)-4-[(3-prop-2-ynyl-ureido)-methyl]-benzamide,
4-{3-[4-(2-amino-phenylcarbamoyl)-benzyl]-ureido}-butyric acid methyl ester.

Yet another embodiment of the invention are compounds of formula I, wherein
A represents pyridin-2,5-diyl;
$R^1$ is a group —$NR^3R^4$, wherein
$R^3$ is hydrogen, and
$R^4$ is —(CH2)$_n$—(O)-alkyl;
n is 1–6;

and pharmaceutically acceptable salts thereof.
One example of such a compound is N-(2-amino-phenyl)-6-[3-(3-butoxy-propyl)-ureidomethyl]-nicotinamide.

Yet another embodiment of the invention are compounds of formula I, wherein
A represents pyridin-2,5-diyl;
$R^1$ represents alkenyl; or
—($CH_2$)$_n$—O-alkyl;
n is 1–6;

and pharmaceutically acceptable salts thereof.
Such compounds include, for example:
N-(2-amino-phenyl)-6-[(2-methoxy-acetylamino)-methyl]-nicotinamide,
N-(2-amino-phenyl)-6-(pent-4-enoylamino-methyl)-nicotinamide.

Yet another embodiment of the invention are compounds of formula I, wherein
A represents thiophen-2,5-diyl;
pyridin-2,5-diyl; or
1,4-phenylene;
$R^1$ is a group —$NR^3R^4$, wherein
$R^3$ is hydrogen;
$R^4$ is alkyl which is unsubstituted or substituted once or several times by halogen;
—NH-alkyl; or
—N(alkyl)$_2$;

and pharmaceutically acceptable salts thereof.
Such compounds include, for example:
5-[3-(2-dimethylamino-ethyl)-ureidomethyl]-thiophene-2-carboxylic acid (2-amino-phenyl)-amide,
5-[3-(2-diisopropylamino-ethyl)-ureidomethyl]-thiophene-2-carboxylic acid (2-amino-phenyl)-amide,
5-[3-(3-diethylamino-propyl)-ureidomethyl]-thiophene-2-carboxylic acid (2-amino-phenyl)-amide,
5-[3-(3-dimethylamino-2,2-dimethyl-propyl)-ureidomethyl]-thiophene-2-carboxylic acid (2-amino-phenyl)-amide,
5-[3-(1-methyl-hexyl)-ureidomethyl]-thiophene-2-carboxylic acid (2-amino-phenyl)-amide,
5-(3-sec-butyl-ureidomethyl)-thiophene-2-carboxylic acid (2-amino-phenyl)-amide,
5-[3-(2-methyl-butyl)-ureidomethyl]-thiophene-2-carboxylic acid (2-amino-phenyl)-amide,
5-(3-isobutyl-ureidomethyl)-thiophene-2-carboxylic acid (2-amino-phenyl)-amide,
5-[3-(3-dibutylamino-propyl)-ureidomethyl]-thiophene-2-carboxylic acid (2-amino-phenyl)-amide,
N-(2-amino-phenyl)-4-[(3-pentyl-ureido)-methyl]-benzamide,
N-(2-amino-phenyl)-4-[3-(3-diethylamino-propyl)-ureidomethyl]-benzamide,
N-(2-amino-phenyl)-4-[3-(3-dimethylamino-2,2-dimethyl-propyl)-ureidomethyl]-benzamide,
N-(2-amino-phenyl)-4-[3-(1-methyl-hexyl)-ureidomethyl]-benzamide,
N-(2-amino-phenyl)-4-[3-(3-dibutylamino-propyl)-ureidomethyl]-benzamide,
N-(2-amino-phenyl)-4-[3-(2-dimethylamino-ethyl)-ureidomethyl]-benzamide,
N-(2-amino-phenyl)-4-[3-(2-diisopropylamino-ethyl)-ureidomethyl]-benzamide, N-(2-amino-phenyl)-4-[3-(2-methyl-butyl)-ureidomethyl]-benzamide,
N-(2-amino-phenyl)-4-(3-isobutyl-ureidomethyl)-benzamide,
N-(2-amino-phenyl)-4-(3-sec-butyl-ureidomethyl)-benzamide,
N-(2-amino-phenyl)-6-[(3-pentyl-ureido)-methyl]-nicotinamide,
N-(2-amino-phenyl)-6-[3-(1-methyl-hexyl)-ureidomethyl]-nicotinamide.

Yet another embodiment of the invention are compounds of formula I, wherein
A represents thiophen-2,5-diyl;
  pyridin-2,5-diyl; or
  1,4-phenylene;
$R^1$ represents alkyl; wherein
  the alkyl group is unsubstituted or substituted once or several times by halogen;
  —NH-alkyl; or
  —N(alkyl)$_2$;

and pharmaceutically acceptable salts thereof.
Such compounds include, for example:
5-[(4-methyl-pentanoylamino)-methyl]-thiophene-2-carboxylic acid (2-amino-phenyl)-amide,
5-(propionylamino-methyl)-thiophene-2-carboxylic acid (2-amino-phenyl)-amide,
5-(butyrylamino-methyl)-thiophene-2-carboxylic acid (2-amino-phenyl)-amide,
5-(isobutyrylamino-methyl)-thiophene-2-carboxylic acid (2-amino-phenyl)-amide,
5-[(2,2,3,3,3-pentafluoro-propionylamino)-methyl]-thiophene-2-carboxylic acid (2-amino-phenyl)-amide,
5-[(2-ethyl-butyrylamino)-methyl]-thiophene-2-carboxylic acid (2-amino-phenyl)-amide,
5-[(2,2,2-trifluoro-acetylamino)-methyl]-thiophene-2-carboxylic acid (2-amino-phenyl)-amide,
5-[(4-dimethylamino-butyrylamino)-methyl]-thiophene-2-carboxylic acid (2-amino-phenyl)-amide,
5-[(3-methyl-butyrylamino)-methyl]-thiophene-2-carboxylic acid (2-amino-phenyl)-amide,
5-[(2-dipropylamino-propionylamino)-methyl]-thiophene-2-carboxylic acid (2-amino-phenyl)-amide,
5-[(2-dimethylamino-acetylamino)-methyl]-thiophene-2-carboxylic acid (2-amino-phenyl)-amide,
5-[(3-methyl-pentanoylamino)-methyl]-thiophene-2-carboxylic acid (2-amino-phenyl)-amide,
N-(2-amino-phenyl)-4-(propionylamino-methyl)-benzamide,
N-(2-amino-phenyl)-4-(isobutyrylamino-methyl)-benzamide,
N-(2-amino-phenyl)-4-[(4-methyl-pentanoylamino)-methyl]-benzamide,
N-(2-amino-phenyl)-4-[(2-ethyl-butyrylamino)-methyl]-benzamide,
N-(2-amino-phenyl)-4-(butyrylamino-methyl)-benzamide,
N-(2-Amino-phenyl)-6-[(4-methyl-pentanoylamino)-methyl]-nicotinamide,
N-(2-Amino-phenyl)-6-[(3-methyl-pentanoylamino)-methyl]-nicotinamide.

Yet another embodiment of the invention are compounds of formula I, wherein
A represents thiophene-diyl, phenylene or pyridine-diyl;
$R^1$ represents a group —NR$^3$R$^4$, wherein R$^3$ and R$^4$ independently represent alkyl, alkenyl or alkynyl which are all optionally substituted; or
  —CH$_2$—(O—CH$_2$—CH$_2$—)$_m$O-alkyl;
  —(CH$_2$)$_n$—(O)-alkyl;
  —(CH$_2$)$_n$—C(O)—NH-alkyl;
  —(CH$_2$)$_n$—NH—C(O)-alkyl;
  —(CH$_2$)$_n$—C(O)alkyl;
  —(CH$_2$)$_n$—C(O)—O-alkyl; or
  —(CH$_2$)$_n$—O—C(O)-alkyl;
n is 1–6;
m is 1–4;

and pharmaceutically acceptable salts thereof.

Yet another embodiment of the invention are compounds of formula I, wherein
A represents 1,4-phenylene;
$R^1$ is a group —NR$^3$R$^4$, wherein R$^3$ and R$^4$ independently represent alkyl;

and pharmaceutically acceptable salts thereof.
One example of such a compound is N-(2-amino-phenyl)-4-(3-butyl-3-methyl-ureidomethyl)-benzamide.

Yet another embodiment of the invention are compounds of formula I-A

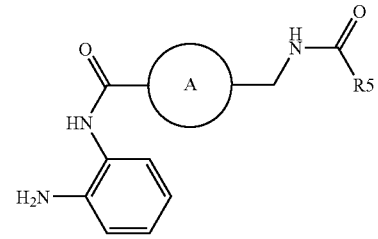

I-A,
wherein
A represents thiophen-2,5-diyl;
  pyridin-2,5-diyl; or
  1,4-phenylene;
$R^5$ represents —(CH$_2$)$_k$-cyclopropyl;
  —(CH$_2$)$_k$-cyclopentyl;
  —(CH$_2$)$_k$-cyclohexyl;
  —(CH$_2$)$_k$-cyclopent-2-enyl;
  —(CH$_2$)$_k$-(5-oxo-pyrrolidin-2-yl);
  —(CH$_2$)$_k$-(2-oxo-pyrrolidin-1-yl);
  —NH—(CH$_2$)$_k$-cyclopropyl;
  —NH—(CH$_2$)$_k$-cyclopentyl;
  —NH—(CH$_2$)$_k$-cyclohexyl;
  —NH—(CH$_2$)$_k$-cyclopent-2-enyl;
  —NH—(CH$_2$)$_k$-(5-oxo-pyrrolidin-2-yl); or
  —NH—(CH$_2$)$_k$-(2-oxo-pyrrolidin-1-yl);
k is 0–6;

and pharmaceutically acceptable salts thereof.
Such compounds include, for example:
5-[(cyclopentanecarbonyl-amino)-methyl]-thiophene-2-carboxylic acid (2-amino-phenyl)-amide,
5-[(2-cyclopent-2-enyl-acetylamino)-methyl]-thiophene-2-carboxylic acid (2-amino-phenyl)-amide,
5-oxo-pyrrolidine-2-carboxylic acid [5-(2-amino-phenylcarbamoyl)-thiophen-2-ylmethyl]-amide,
5-[(3-cyclopentyl-propionylamino)-methyl]-thiophene-2-carboxylic acid (2-amino-phenyl)-amide,
5-[(3-cyclohexyl-propionylamino)-methyl]-thiophene-2-carboxylic acid (2-amino-phenyl)-amide,
5-[(2-cyclopentyl-acetylamino)-methyl]-thiophene-2-carboxylic acid (2-amino-phenyl)-amide, 5-[(2-cyclopropyl-acetylamino)-methyl]-thiophene-2-carboxylic acid (2-amino-phenyl)-amide,
5-{3-[3-(2-oxo-pyrrolidin-1-yl)-propyl]-ureidomethyl}-thiophene-2-carboxylic acid (2-amino-phynyl)-amide,
N-(2-amino-phenyl)-4-[(cyclopentanecarbonyl-amino)-methyl]-benzamide,
N-(2-amino-phenyl)-4-[(2-cyclopent-2-enyl-acetylamino)-methyl]-benzamide,
N-(2-amino-phenyl)-4-[(3-cyclopentyl-propionylamino)-methyl]-benzamide,
N-(2-amino-phenyl)-4-{3-[3-(2-oxo-pyrrolidin-1-yl)-propyl]-ureidomethyl}-benzamide,
N-(2-amino-phenyl)-4-(3-cyclopropylmethyl-ureidomethyl)-benzamide,
N-(2-amino-phenyl)-6-[(3-cyclopentyl-propionylamino)-methyl]-nicotinamide,
N-(2-Amino-phenyl)-6-{3-[3-(2-oxo-pyrrolidin-1-yl)-propyl]-ureidomethyl}-nicotinamide,
N-(2-Amino-phenyl)-6-[(2-cyclopent-2-enyl-acetylamino)-methyl]-nicotinamide,
N-(2-Amino-phenyl)-6-[(2-cyclopentyl-acetylamino)-methyl]-nicotinamide,
N-(2-Amino-phenyl)-6-[(3-cyclohexyl-propionylamino)-methyl]-nicotinamide.

A further embodiment of the invention is the process for the manufacture of the present (acylamino-methyl)-arylene-carboxylic acid (2-amino-phenyl)-amide derivatives of the formula I, or a pharmaceutically-acceptable salt thereof, said process comprising:

(a) reacting a compound of formula II

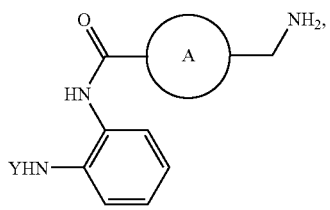

II wherein A has the meaning defined above and Y represents a suitable protecting group, with a compound of the general formula III

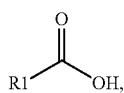

III wherein
R¹ is alkyl, alkenyl, alkynyl which are all optionally substituted; or
—CH₂—(O—CH₂—CH₂—)ₘO-alkyl;
—(CH₂)ₙ—O-alkyl;
—(CH₂)ₙ—C(O)—NH-alkyl;
—(CH₂)ₙ—NH—C(O)-alkyl;
—(CH₂)ₙ—C(O)alkyl;
—(CH₂)ₙ—C(O)—O-alkyl; or
—(CH₂)ₙ—O—C(O)-alkyl;

or reacting said compound of formula II with a compound of formula X

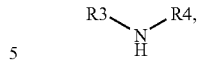

X wherein R³ and R⁴ independently represent hydrogen;

alkyl, alkenyl, alkynyl which are all optionally substituted; or
—CH₂—(O—CH₂—CH₂—)ₘO-alkyl;
—(CH₂)ₙ—O-alkyl;
—(CH₂)ₙ—C(O)—NH-alkyl;
—(CH₂)ₙ—NH—C(O)-alkyl;
—(CH₂)ₙ—C(O)alkyl;
—(CH₂)ₙ—C(O)—O-alkyl; or
—(CH₂)ₙ—O—C(O)-alkyl;

n is 1–6;

m is 1–4;

(b) subsequent cleavage of the protection group; and (c) if desired, turning the product into a pharmaceutically acceptable salt by addition of a suitable acid or base.

Necessary starting materials for the above-mentioned process may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

Protection groups for the amino group in process step (a) and methods for their cleavage (process step (b)) are known from peptide chemistry. Examples include benzyloxycarbonyl (cleavage by hydrogenation or hydrobromic acid in acetic acid), t-butoxycarbonyl (cleavage by strong acids such as trifluoroacetic acid, neat or in dichloromethane, or hydrochloric acid (HCl) in dioxane), 9-fluorenmethoxycarbonyl (cleavage by secondary amines, such as, piperidine).

The manufacture of compounds of the general formula I will now be described in detail and according to the nature of the group A, as well as the cases wherein R¹ is or is not a group —NR³R⁴ as defined above.

The reaction of compounds of formula II with compounds of formula III wherein R¹ is not a group —NR³R⁴ typically involves a three-step one-pot procedure. In the first step, the carboxylate of the formula III becomes activated. This reaction is carried out in an inert solvent or diluent, for example in dichloromethane, dioxane or tetrahydrofuran (THF) and in the presence of an activating agent. A suitable reactive derivative of an acid is, for example, an acyl halide, for example an acyl chloride formed by the reaction of the acid and an inorganic acid chloride, for example thionyl chloride or oxalic acid dichloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N-3-dimethylaminopropyl-N-ethylcarbodiimid or dicyclohexylcarbodiimide, or the product of the reaction of the acid with N,N'-carbonyldiimidazole; or the product of the reaction of the acid and uronium salts such as O-(1H-benzotriazol-1-yl)-N,N,N',N',-tetramethyluronium tetrafluoro-borate; or the product of the reaction of the acid and phosphorus based reagents, e.g. bis-(2-oxo-3-oxazolidinyl)-phosphorylchloride.

In the second step, a compound of formula II is added to the solution. These methods are well known to those skilled in the art. In principle, all methods for the synthesis of amides as used in peptide chemistry as described in e.g. Houben-Weyl, "Methoden der organischen Chemie", Vol. XV/1 and XV/2 are also applicable.

If Y is t-butoxycarbonyl, it can be finally cleaved in the third step by addition of trifluoroacetic acid to the reaction mixture to yield compounds of formula I. Alternatively the amide product is isolated after the second step and the cleavage of the protecting group Y is carried out in a separate step under reaction conditions as described above. The preparation of compound II wherein A is phenyl and Y is t-butoxycarbonyl ([2-(4-Aminomethyl-benzoylamino)-phenyl]-carbamic acid t-butyl ester) is described in the literature, e.g. EP 0 847 992.

A preferred method for the preparation of compounds of the formula II, wherein A is 2,5-thiophene, involves the removal of the allyl groups of compounds IV

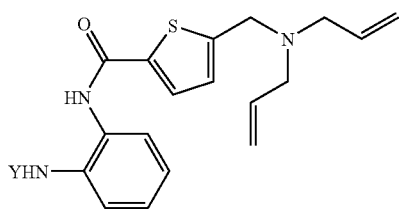

The cleavage of the allyl groups can be accomplished for example by palladium-catalyzed reaction in the presence of sulfinic acids, carboxylic acids, morpholine, dimedone or N,N'-dimethylbarbituric acid as allyl scavengers.

The compounds of formula IV can be obtained by the reaction of compound V

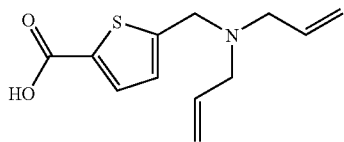

with a compound of the formula VI

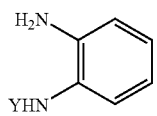

wherein Y represents suitable protecting group as defined above.

This reaction typically involves a two-step, one-pot procedure. In the first step, the carboxylate of compound V becomes activated. This reaction is carried out in an inert solvent or diluent (for example, in dichloromethane, dioxane or THF) and in the presence of an activating agent. A suitable reactive derivative of an acid is, for example, an acyl halide, for example an acyl chloride formed by the reaction of the acid and an inorganic acid chloride, for example thionyl chloride or oxalic acid dichloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N-3-dimethylaminopropyl-N-ethylcarbodiimid or dicyclohexylcarbodiimide, or the product of the reaction of the acid with N,N'-carbonyldiimidazole; or the product of the reaction of the acid and uronium salts such as O-(1H-benzotriazol-1-yl)-N,N,N',N',-tetramethyluronium tetrafluoro-borate; or the product of the reaction of the acid and phosphorus based reagents, e.g. bis-(2-oxo-3-oxazolidinyl)-phosphorylchloride.

In the second step, compound VI is added to the solution to yield compound IV.

These methods are well known to those skilled in the art. In principle, all methods for the synthesis of amides as used in peptide chemistry as described in e.g. Houben-Weyl, "Methoden der organischen Chemie", Vol. XV/1 and XV/2 are also applicable.

The compounds of formula V are prepared by hydrolysis from compounds of the formula VII.

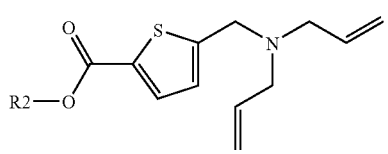

wherein $R^2$ is alkyl or optionally substituted benzyl. Alkyl as used herein has the significance given before. Examples for $R^2$ are methyl, ethyl, t-butyl, benzyl or p-methoxybenzyl. The conditions under which the hydrolysis is carried out depend on the nature of the group $R^2$. When $R^2$ is a methyl or ethyl group, the reaction is carried out in the presence of a base, for example, lithium hydroxide, sodium hydroxide, or potassium hydroxide in an inert solvent or diluent, for example in methanol, ethanol, dioxane, THF, water. When $R^2$ is the t-butyl group, the reaction is carried out in the presence of an acid, for example, a solution of hydrochloric acid in an inert solvent such as diethyl ether or dioxane, or trifluoroacetic acid in dichloromethane. When $R^2$ is the benzyl group, the reaction is carried out by hydrogenolysis in the presence of a noble metal catalyst such as palladium or platinum on a suitable carrier, such as carbon.

5-Diallylaminomethyl-thiophene-2-carboxylic esters are described in the literature, in e.g. Millot, N., et al., Synthesis 7 (2000) 941–948.

One preferred method for the production of compounds of the formula II wherein A is 2,5-pyridine involves the reduction of the cyano group of compound VIII.

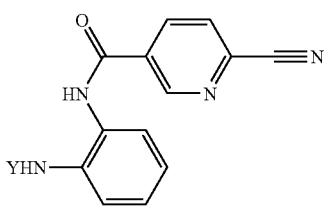

VIII

The reduction of the nitrile can be accomplished, for example, by hydrogen in the presence of a catalyst, e.g. palladium on carbon or Raney-nickel, in a suitable solvent, e.g. THF, methanol, ethanol or dimethyl formamide (DMF), optionally in the presence of, e.g., HCl, triethylamine, ammonia or hydroxylamine.

One preferred method for the production of compounds of the formula VIII involves the reaction of compound IX

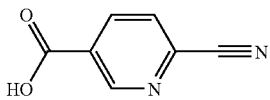

IX with a compound of the formula VI

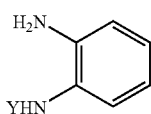

VI wherein Y represents suitable protecting group as defined above. The reaction can be carried out under conditions as described for the preparation of compound IV. 6-Cyanonicotinic acid is described in the literature, in e.g. Vorbrueggen, H., and Krolikiewicz, K., Synthesis 4 (1983) 316–319.

The ureidomethyl derivatives of the general formula I in which $R^1$ is a group —$NR^3R^4$ as defined herein before may be prepared by any process known to be applicable to the preparation of chemically-related compounds. Such processes are illustrated by the following representative examples. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

One preferred method for the production of said ureidomethyl derivatives of formula I involves the reaction of compounds of the formula II wherein Y is preferably t-butoxycarbonyl with an amine of the formula X

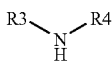

X wherein $R^3$ and $R^4$ have the meaning defined above.

This reaction typically involves a three-step, one-pot procedure. In the first step, compound X is reacted with carbonyldiimidazol in an appropriate solvent, e.g. THF. In the second step, compound II is added to the reactive intermediate to form the corresponding ureido derivative. Finally, Y is cleaved by addition of trifluoroacetic acid to the reaction mixture to yield the ureidomethyl derivatives of formula I.

Alternatively, the ureido product is isolated after the second step and the cleavage of the protecting group Y is carried out in a separate step under reaction conditions as described above.

If Y is t-butoxycarbonyl, it can be finally cleaved in the third step by addition of trifluoroacetic acid to the reaction mixture to yield said derivatives of formula I.

The compounds of the general formula I can contain one or several chiral centers and can then be present in a racemic or in an optically active form. The racemates can be separated according to known methods into the enantiomers. For instance, diastereomeric salts, which can be separated by crystallization, are formed from the racemic mixtures by reaction with an optically active acid such as D- or L-tartaric acid, mandelic acid, malic acid, lactic acid or camphorsulfonic acid. Alternatively, separation of the enantiomers can also be achieved by using chromatography on chiral High Performance Liquid Chromatography (HPLC)-phases which are commercially available.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethylammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Ansel, H., et. al., Pharmaceutical Dosage Forms and Drug Delivery Systems, 6th ed., 1995, pp. 196 and 1456–1457.

The compounds according to this invention and their pharmaceutically acceptable salts can be used as medicaments, e.g., in the form of pharmaceutical preparations. The pharmaceutical preparations can be administered orally, e.g., in the form of tablets, coated tablets, dragées, hard and soft gelatine capsules, solutions, emulsions or suspensions. The administration can, however, also be effected rectally, e.g., in the form of suppositories, or parenterally, e.g., in the form of injection solutions.

The above-mentioned pharmaceutical preparations can be obtained by processing the compounds according to this invention with pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The activity of the compounds according to this invention as HDAC inhibitors is demonstrated using a cellular acetylation assay. Therein, acetylation of histones is monitored in PC3 cells. High acetylation means inhibition of histone deacetylase by compounds. Cell viability is monitored in parallel to estimate the cytotoxicity of the compounds.

PC3 cells, human prostate carcinoma cells, are seeded as 1800 cells per well of 384-well microtiterplate in RPMI 1640 (including 5% FCS, 2 mM glutamine and pen/strep). After 48 h at 37° C., pre-diluted compounds are added at a final concentration of 1 uM. Compounds are pre-diluted 1:10 in dimethyl sulfoxide (DMSO) or medium resulting in a final concentration of DMSO of 0.5%.

After 24 h, incubation the cell viability is determined by adding cell proliferation reagent WST1. Another 60 min. later, the optical density (OD) is measured (450 nm versus 690 nm).

After WST1 assay, the cell layer is prepared for the ELISA reaction. Medium is aspirated and cells are fixed in ethanol at −20° C. for 60 min. After washing with PBS/Tween, the blocking solution (PBS/ 5% FCS/Tween) is added and the cell layer is washed again. Antibodies against histone H3 or H4 (Anti-Acetylated Histone (rabbit polyclonal IgG), Upstate Biotechnologie) are added at a dilution of 1:200 for 60 min at 37° C. As a second antibody, goat anti-rabbit IgG(H+L) human IgG adsorbed-HRP conjugate (Dako) is used (1:2000 diluted). Cells are washed 3 times and the peroxidase substrate ABTS is allowed to react for 30–60 min at 37° C. Oxalic acid stops the reaction, and the OD is measured at 405 nm.

The percentage of acetylation is calculated after subtraction of blank O.D.s:

$$\frac{\frac{\text{mean } O.D. \text{ acetylation}}{\text{mean } O.D. \text{ WSTI}}}{\text{mean } O.D. \text{ DMSO control}} * 100\%$$

| Example No. | Compound Name | cell acetylation (PC3, 1 μM) [% of control] |
|---|---|---|
| | Reference Compound CI 994 | 152 |
| 4-1 | 5-[(4-Methyl-pentanoylamino)-methyl]-thiophene-2-carboxylic acid (2-amino-phenyl)-amide | 170 |
| 4-3 | 5-[(2-Ethoxy-acetylamino)-methyl]-thiophene-2-carboxylic acid (2-amino-phenyl)-amide | 194 |
| 4-6 | 5-(Butyrylamino-methyl)-thiophene-2-carboxylic acid (2-amino-phenyl)-amide | 238 |
| 6-8 | 5-[3-(2-Methyl-butyl)-ureidomethyl]-thiophene-2-carboxylic acid (2-amino-phenyl)-amide | 198 |
| 6-12 | 5-[(3-Allyl-ureido)-methyl]-thiophene-2-carboxylic acid (2-amino-phenyl)-amide | 170 |
| 6-13 | 5-(3-Isobutyl-ureidomethyl)-thiophene-2-carboxylic acid (2-amino-phenyl)-amide | 178 |
| 4-31 | N-(2-Amino-phenyl)-4-[(2-cyclopent-2-enyl-acetylamino)-methyl]-benzamide | 176 |
| 6-19 | N-(2-Amino-phenyl)-4-[3-(3-dimethylamino-2,2-dimethyl-propyl)-ureidomethyl]-benzamide | 205 |
| 6-25 | N-(2-Amino-phenyl)-4-[3-(1-methyl-hexyl)-ureidomethyl]-benzamide | 192 |
| 6-26 | N-(2-Amino-phenyl)-4-[3-(3-ethoxy-propyl)-ureidomethyl]-benzamide | 179 |
| 6-27 | 4-[(3-Allyl-ureido)-methyl]-N-(2-amino-phenyl)-benzamide | 175 |
| 6-28 | N-(2-Amino-phenyl)-4-[3-(3-isopropoxy-propyl)-ureidomethyl]-benzamide | 177 |
| 6-29 | N-(2-Amino-phenyl)-4-(3-cyclopropylmethyl-ureidomethyl)-benzamide | 187 |
| 6-38 | N-(2-Amino-phenyl)-6-[(3-pentyl-ureido)-methyl]-nicotinamide | 178 |

The effect of the compounds according to the invention may further be assessed by the following test:

Method

Male NMRI nu/nu-mice (n=15 per group), aged 8–10 weeks, were subcutaneously injected with $5*10^6$ PC-3 prostate carcinoma cells. On day 10, animals with tumor volumes of about 150 mm$^3$ were randomly assigned to treatment groups. The test compound was administered as a microsuspension in 7.5% Gelatine-0.22% NaCl-Suspension with an application volume of 10 ml/kg based on actual body weights. Once daily oral treatment was performed from approximately day 10 to day 27 on a 5–7 times per week treatment schedule. The volume of the tumor is determined from the following equation:

Volume of a tumor=½ab², where "a" and "b" are the long and the short diameters of the tumor, respectively, The invention will now be illustrated in the following non-limiting examples in which, unless otherwise stated:

i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany;

(iv) yields are given for illustration only and are not necessarily the maximum attainable;

(v) melting points were determined using a Mettler SP62 automatic melting point apparatus, an oil-bath apparatus or a Kofler hot plate apparatus.

(vi) the structures of the end-products of the formula I were confirmed by nuclear (generally proton) magnetic resonance (NMR) and mass spectral techniques (Micromass Platform II machine using APCI or Micromass Platform ZMD using electrospray);

(vii) intermediates were not generally fully characterized and purity was assessed by thin layer chromatography;

(viii) the following abbreviations have been used:

| | |
|---|---|
| DMF | N,N-dimethyl formamide; |
| DMSO | dimethyl sulfoxide; |
| THF | tetrahydrofuran; |
| MeOH | methanol; |
| HCl | hydrochloric acid; |
| NaH | sodium hydride |
| $CH_2Cl_2$ | dichloromethane; |
| $H_2SO_4$ | sulfuric acid |
| sat. | saturated |
| sol. | solution |
| rt | room temperature |
| eq | equivalent |
| $MW_{found}$ | molecular weight (as determined by mass spectrometry) |
| $MW_{calc'd}$ | molecular weight (as calculated from the chemical formula) |

EXAMPLE 1

Step 1: {2-[(6-Cyano-pyridine-3-carbonyl)-amino]-phenyl}-carbamic Acid t-butyl Ester To a solution of 444 mg (3.0 mmol) 6-cyano-nicotinic acid and 354 mg (3.5 mmol) N-methylmorpholine in 7 ml DMF at −20° C. was added 450 mg (3.3 mmol) isobutyl chloroformate. The reaction mixture was warmed to 5° C., and 625 mg (3.0 mmol) mono-boc-ortho-phenylenediamine was added. The reaction mixture was warmed to rt overnight and then poured into 50 ml 5% aqueous citric acid. The aqueous phase was extracted with ethyl acetate, the combined organic phases were washed with bicarbonate and brine and dried over $Na_2SO_4$. The solvent was evaporated and the residue was subjected to silica gel chromatography (petrol ether/ethyl acetate 2:1) to yield 795 mg (2.35 mmol) {2-[(6-Cyano-pyridine-3-carbonyl)-amino]-phenyl}-carbamic acid t-butyl ester; mp.183–184° C.

Step 2: {2-[(6-Aminomethyl-pyridine-3-carbonyl)-amino]-phenyl}-carbamic Acid t-butyl Ester In a flask, 2920 mg (8.72 mmol) {2-[(6-Cyano-pyridine-3-carbonyl)-amino]-phenyl}-carbamic acid t-butyl ester and 1000 mg Pd (10% on carbon) were placed under nitrogen and 10 ml THF and 120 ml methanol were added. The starting material was hydrogenated under atmospheric pressure and at rt for 3.5 h. The catalyst was filtered off. The solvent was evaporated and the residue was subjected to silica gel chromatography (toluene/isopropanol/$NH_3$ (conc.) 16:20:1) to yield 2600 mg (7.6 mmol) {2-[(6-Aminomethyl-pyridine-3-carbonyl)-amino]-phenyl}-carbamic acid t-butyl ester; exact MW [M+H] calc'd: 343.18; MW found [M+H]: 343.2.

EXAMPLE 2

Step 1:
5-Diallylaminomethyl-thiophene-2-carboxylic Acid

To a solution of 4.5 g (17.9 mmol) 5-diallylaminomethyl-thiophene-2-carboxylic acid methyl ester in 45 ml methanol were added to 17.9 ml of a 1 N aqueous solution of KOH (17.9 mmol). The reaction mixture was stirred at 50° C. for 16 h and 1 h at reflux. The solvent was evaporated, 20 ml water was added to the residue and 9 ml of a 2 N aqueous solution of HCl. The aqueous phase was extracted with ethyl acetate, the combined organic phases were dried over $Na_2SO_4$. The solvent was evaporated and the residue was subjected to silica gel chromatography (ethyl acetate) to yield 4.05 g (17.06 mmol) 5-diallylaminomethyl-thiophene-2-carboxylic acid; exact MW [M+H] calc'd: 238.09; MW found [M+H]: 238.3.

Step 2: {2-[(5-Diallylaminomethyl-thiophene-2-carbonyl)-amino]-phenyl}-carbamic Acid t-butyl Ester To a solution of 2.70 g (11.38 mmol) 5-diallylaminomethyl-thiophene-2-carboxylic acid in 50 ml THF was added 2.03 g (12.51 mmol) carbonyldiimidazol. After 45 min at rt, 2.48 g (11.95 mmol) mono-boc-ortho-phenylenediamine were added to the reaction mixture, and it was stirred for 3 h at rt. The solvent was evaporated and the residue dissolved in ethyl acetate. The organic phase was washed twice with sat. $NaHCO_3$, once with water and dried over $Na_2SO_4$. The solvent was evaporated and the residue was subjected to silica gel chromatography (ethyl acetate/heptane 2:8) to yield 4.10 g (9.59 mmol) {2-[(5-Diallylaminomethyl-thiophene-2-carbonyl)-amino]-phenyl}-carbamic acid t-butyl ester; exact MW [M+H] calc'd: 428.20; MW found [M+H]: 428.3.

Step 3: {2-[(5-Aminomethyl-thiophene-2-carbonyl)-amino]-phenyl}-carbamic Acid t-butyl Ester To a solution of 22.35 g (143.13 mmol) N,N'-dimethyl-barbituric acid and 0.55 g (0.477 mmol) tetrakis(triphenylphosphine)palladium (0) in 200 ml $CH_2Cl_2$ were added 10.20 g (23.86 mmol) diallylaminomethyl-thiophene-2-carbonyl)-amino]-phenyl}-carbamic acid t-butyl ester. After 1 h at 35° C., the solvent was evaporated and 0.1 N aqueous HCl was added to the residue. The aqueous phase was extracted three times with diethylether and the combined organic phases were extracted with sat. NaHCO$_3$. The acidic aqueous phase was neutralized with sat. NaHCO$_3$ and the combined aqueous phases were extracted three times with CH$_2$Cl$_2$. The organic phase was dried over Na$_2$SO$_4$. The solvent was evaporated and the residue was subjected to silica gel chromatography (dichloromethane/methanol 9:1) to yield 4.63 g (13.32 mmol) {2-[(5-Aminomethyl-thiophene-2-carbonyl)-amino]-phenyl}-carbamic acid t-butyl ester; exact MW [M+H] calc'd: 348.14; MW found [M+H]: 348.1.

EXAMPLE 3

5-[(3-Methyl-pentanoylamino)-methyl]-thiophene-2-carboxylic Acid (2-amino-phenyl)-amide To a solution of 33.43 mg (0.288 mmol) 3-methylpentanoic acid in 1 ml THF were added 46.67 mg (0.288 mmol) 1,1'-carbonyldiimidazol. After 1 h at rt 100 mg (0.288 mmol) {2-[(5-aminomethyl-thiophene-2-carbonyl)-amino]-phenyl}-carbamic acid t-butyl ester were added and the reaction mixture was stirred for 3 h at rt. 1.7 ml trifluoroacetic acid were added and after 2 h at rt sat. aqueous NaHCO$_3$ was added carefully and the aqueous phase was extracted three times with ethyl acetate. The combined organic phases were dried over Na$_2$SO$_4$. The solvent was evaporated and the residue was subjected to silica gel chromatography (ethyl acetate/heptane 6:4) to yield 59.3 mg (0.171 mmol) 5-[(3-Methyl-pentanoylamino)-methyl]-thiophene-2-carboxylic acid (2-amino-phenyl)-amide; exact MW [M+H] calc'd: 346.16; MW found [M+H]: 346.4.

EXAMPLE 4

In an analogous manner to that described in the example 3, and using known methods as described in the literature (e.g., in standard works such as Houben-Weyl, "Methoden der Organischen Chemie, Georg Thieme Verlag", Stuttgart; Organic Reactions, John Wiley & Sons, Inc., New York), the following compounds are prepared:

| Compound Name | exact MW [M + H] calc'd [g/mol] | MW found [M + H] [g/mol] |
|---|---|---|
| 4-1<br>5-[(Cyclopentanecarbonyl-amino)-methyl]-thiophene-2-carboxylic acid (2-amino-phenyl)-amide | 344.14 | 344.2 |
| 4-2<br>5-[(4-Methyl-pentanoylamino)-methyl]-thiophene-2-carboxylic acid (2-amino-phenyl)-amide<br>$^1$H-NMR (400 MHz, CD$_3$OD): δ=9.63(s, 1H), 8.52(t, J=6.1Hz, 1H), 7.79–7.78(m, 1H), 7.12–7.09(m, 1H), 7.00–6.99 (m, 1H), 6.97–6.95(m, 1H), 6.78–6.76(m, 1H), 6.61–6.57 (m, 1H), 4.42(d, J=6.1Hz, 2H), 2.13(t, J=7.6Hz, 2H), 1.56–1.39(m, 3H), 0.86(d, J=6.1Hz, 6H) | 346.16 | 346.2 |
| 4-3<br>5-[(2-Ethoxy-acetylamino)-methyl]-thiophene-2-carboxylic acid (2-amino-phenyl)-amide<br>$^1$H-NMR (400 MHz, CD$_3$OD): δ=9.63(s, 1H), 8.48(t, J=6.1Hz, 1H), 7.79–7.78(m, 1H), 7.11–7.09(m, 1H), 7.01–7.00 (m, 1H), 6.99–6.95(m, 1H), 6.78–6.76(m, 1H), 6.61–6.56 (m, 1H), 4.89(s, 2H), 4.47(d, J=6.1Hz, 2H), 3.89(s, 2H), 3.50(q, J=6.9Hz, 2H), 1.16(t, J=6.8Hz, 3H) | 334.12 | 334.1 |
| 4-4<br>5-(Propionylamino-methyl)-thiophene-2-carboxylic acid (2-amino-phenyl)-amide | 304.11 | 304.2 |
| 4-5<br>5-(Pent-4-enoylamino-methyl)-thiophene-2-carboxylic acid (2-amino-phenyl)-amide | 330.13 | 330.3 |
| 4-6<br>5-(Butyrylamino-methyl)-thiophene-2-carboxylic acid (2-amino-phenyl)-amide | 318.13 | 317.9 |
| 4-7<br>5-(Isobutyrylamino-methyl)-thiophene-2-carboxylic acid (2-amino-phenyl)-amide | 340.11 [M + Na] | 340.0 [M + Na] |
| 4-8<br>5-[(2,2,3,3,3-Pentafluoro-propionylamino)-methyl]-thiophene-2-carboxylic acid (2-amino-phenyl)-amide | 394.06 | 394.1 |
| 4-9<br>5-[(2-Acetylamino-acetylamino)-methyl]-thiophene-2-carboxylic acid (2-amino-phenyl)-amide | 347.12 | 347.2 |
| 4-10<br>5-[(2-Ethyl-butyrylamino)-methyl]-thiophene-2-carboxylic acid (2-amino-phenyl)-amide | 346.16 | 346.2 |
| 4-11<br>5-[(2-Cyclopent-2-enyl-acetylamino)-methyl]-thiophene-2-carboxylic acid (2-amino-phenyl)-amide<br>$^1$H-NMR (400 MHz, CD$_3$OD): δ=9.62(s, 1H), 8.53(t, J=5.8Hz, 1H), 7.79–7.78(m, 1H), 7.12–7.10(m, 1H), 7.01–7.00 | 356.14 | 356.2 |

| Compound Name | exact MW [M + H] calc'd [g/mol] | MW found [M + H] [g/mol] |
|---|---|---|
| (m, 1H), 6.99–6.95(m, 1H), 6.78–6.76(m, 1H), 6.61–6.57 (m, 1H), 5.75–5.72(m, 1H), 5.68–5.65(m, 1H), 4.88(s, 2H), 4.44(d, J=5.6Hz, 2H), 3.04–2.95(m, 1H), 2.36–1.94 (m, 5H), 1.45–1.37(m, 1H) | | |
| 4-12 5-({2-[2-(2-Methoxy-ethoxy)-ethoxy]-acetylamino}-methyl)-thiophene-2-carboxylic acid (2-amino-phenyl)-amide | 408.16 | 408.2 |
| 4-13 5-[(4-Oxo-pentanoylamino)-methyl]-thiophene-2-carboxylic acid (2-amino-phenyl)-amide | 346.12 | 346.2 |
| 4-14 5-Oxo-pyrrolidine-2-carboxylic acid [5-(2-amino-phenylcarbamoyl)-thiophen-2-ylmethyl]-amide | 359.12 | 359.2 |
| 4-15 5-[(2,2,2-Trifluoro-acetylamino)-methyl]-thiophene-2-carboxylic acid (2-amino-phenyl)-amide | 344.07 | 344.1 |
| 4-16 5-[(4-Dimethylamino-butyrylamino)-methyl]-thiophene-2-carboxylic acid (2-amino-phenyl)-amide | 361.17 | 361.2 |
| 4-17 5-[(3-Cyclopentyl-propionylamino)-methyl]-thiophene-2-carboxylic acid (2-amino-phenyl)-amide $^1$H-NMR (400 MHz, CD$_3$OD): δ=9.63(s, 1H), 8.52(t, J=6.1Hz, 1H), 7.79–7.78(m, 1H), 7.11–7.09(m, 1H), 7.00–6.99 (m, 1H), 6.97–6.95(m, 1H), 6.78–6.76(m, 1H), 6.61–6.57 (m, 1H), 4.89(s, 2H), 4.42(d, J=5.6Hz, 2H), 2.13(t, J=7.6Hz, 2H), 1.76–1.67(m, 3H), 1.60–1.44(m, 6H), 1.10–1.00(m, 2H) | 372.17 | 372.2 |
| 4-18 5-[(3-Cyclohexyl-propionylamino)-methyl]-thiophene-2-carboxylic acid (2-amino-phenyl)-amide | 386.19 | 386.3 |
| 4-19 5-[(3-Methyl-butyrylamino)-methyl]-thiophene-2-carboxylic acid (2-amino-phenyl)-amide | 332.14 | 332.3 |
| 4-20 5-[(2-Dipropylamino-propionylamino)-methyl]-thiophene-2-carboxylic acid (2-amino-phenyl)-amide | 403.22 | 403.4 |
| 4-21 5-[(2-Dimethylamino-acetylamino)-methyl]-thiophene-2-carboxylic acid (2-amino-phenyl)-amide | 333.14 | 333.3 |
| 4-22 5-[(2-Cyclopentyl-acetylamino)-methyl]-thiophene-2-carboxylic acid (2-amino-phenyl)-amide | 358.16 | 358.3 |
| 4-23 5-[(2-Cyclopropyl-acetylamino)-methyl]-thiophene-2-carboxylic acid (2-amino-phenyl)-amide | 330.13 | 330.3 |
| 4-24 N-(2-Amino-phenyl)-4-[(cyclopentanecarbonyl-amino)-methyl]-benzamide | 338.19 | 338.3 |
| 4-25 N-(2-Amino-phenyl)-4-(propionylamino-methyl)-benzamide | 298.16 | 298.3 |
| 4-26 N-(2-Amino-phenyl)-4-(isobutyrylamino-methyl)-benzamide | 312.17 | 312.4 |
| 4-27 N-(2-Amino-phenyl)-4-[(2-ethoxy-acetylamino)-methyl]-benzamide | 328.17 | 328.3 |
| 4-28 N-(2-Amino-phenyl)-4-(pent-4-enoylamino-methyl)-benzamide | 324.17 | 324.3 |
| 4-29 N-(2-Amino-phenyl)-4-[(4-methyl-pentanoylamino)-methyl]-benzamide | 340.2 | 340.3 |
| 4-30 N-(2-Amino-phenyl)-4-[(2-ethyl-butyrylamino)-methyl]-benzamide $^1$H-NMR (400 MHz, (CD$_3$)$_2$CO): δ=9.62(s, 1H), 8.44(t, J= 5.8Hz, 1H), 7.94–7.92(m, 2H), 7.39–7.36(m, 2H), 7.17–7.15 (m, 1H), 6.99–6.95(m, 1H), 6.79–6.77(m, 1H), 6.61–6.58 (m, 1H), 4.89(s, 2H), 4.36(d, J=5.6Hz, 2H), 2.11–2.01 (m, 1H), 1.55–1.33(m, 4H), 0.81(t, J=7.3Hz, 6H) | 340.2 | 340.4 |

-continued

| Compound Name | exact MW [M + H] calc'd [g/mol] | MW found [M + H] [g/mol] |
|---|---|---|
| 4-31 N-(2-Amino-phenyl)-4-[(2-cyclopent-2-enyl-acetylamino)-methyl]-benzamide $^1$H-NMR (400 MHz, (CD$_3$)$_2$CO): δ=9.62(s, 1H), 8.43(t, J=5.8Hz, 1H), 7.95–7.92(m, 2H), 7.37–7.35(m, 2H), 7.17–7.15 (m, 1H), 6.99–6.95(m, 1H), 6.79–6.77(m, 1H), 6.62–6.58 (m, 1H), 5.76–5.66(m, 2H), 4.89(s, 2H), 4.34(d, J=5.1Hz, 2H), 3.04–2.96(m, 1H), 2.37–2.09(m, 4H), 2.04–1.95 (m, 1H), 1.47–1.39(m, 1H) | 350.19 | 350.3 |
| 4-32 N-(2-Amino-phenyl)-4-(butyrylamino-methyl)-benzamide | 310.16 [M − H] | 310.3 [M − H] (AP−) |
| 4-33 N-(2-Amino-phenyl)-4-({2- [2-(2-methoxy-ethoxy)-ethoxy]-acetylamino}-methyl)-benzamide | 400.19 [M−H] | 400.3 [M−H] (AP−) |
| 4-34 4-[(2-Acetylamino-acetylamino)-methyl]-N-(2-amino-phenyl)-benzamide | 341.16 | 341.3 |
| 4-35 N-(2-Amino-phenyl)-4-[(3-cyclopentyl-propionylamino)-methyl]-benzamide | 366.22 | 366.3 |
| 4-36 N-(2-Amino-phenyl)-6-[(2-methoxy-acetylamino)-methyl]-nicotinamide $^1$H-NMR (400 MHz, (CD$_3$)$_2$CO): δ=9.79(s, 1H), 9.10(s, 1H), 8.51(t, J=6.1Hz, 1H), 8.31–8.28(m, 1H), 7.42–7.40 (m, 1H), 7.19–7.17(m, 1H), 7.02–6.98(m, 1H), 6.80–6.78 (m, 1H), 6.63–6.59(m, 1H), 4.99(br s, 2H), 4.50(d, J=5.6Hz, 2H), 3.94(s, 2H), 3.39(s, 3H) | 315.15 | 315.2 |
| 4-37 N-(2-Amino-phenyl)-6-(pent-4-enoylamino-methyl)-nicotinamide $^1$H-NMR (400 MHz, (CD$_3$)$_2$CO): δ=9.78(s, 1H), 9.05(s, 1H), 8.55(t, J=5.8Hz, 1H), 8.29–8.26(m, 1H), 7.39–7.37 (m, 1H), 7.17–7.15(m, 1H), 7.00–6.96(m, 1H), 6.79–6.76 (m, 1H), 6.61–6.57(m, 1H), 5.89–5.79(m, 1H), 5.08–4.97 (m, 2H), 4.97(s, 2H), 4.42(d, J=6.1Hz, 2H), 2.30–2.29(m, 4H) | 325.17 | 325.2 |
| 4-38 N-(2-Amino-phenyl)-6-[(3-cyclopentyl-propionylamino)-methyl]-nicotinamide | 367.21 | 367.2 |
| 4-39 N-(2-Amino-phenyl)-6-[(2-cyclopent-2-enyl-acetylamino)-methyl]-nicotinamide | 351.18 | 351.2 |
| 4-40 N-(2-Amino-phenyl)-6-[(4-methyl-pentanoylamino)-methyl]-nicotinamide | 341.20 | 341.2 |
| 4-41 N-(2-Amino-phenyl)-6-[(3-methyl-pentanoylamino)-methyl]-nicotinamide | 341.20 | 341.2 |
| 4-42 N-(2-Amino-phenyl)-6-[(2-cyclopentyl-acetylamino)-methyl]-nicotinamide | 353.20 | 353.2 |
| 4-43 N-(2-Amino-phenyl)-6-[(3-cyclohexyl-propionylamino)-methyl]-nicotinamide | 381.23 | 381.2 |

EXAMPLE 5

5-[(3-Prop-2-ynyl-ureido)-methyl]-thiophene-2-carboxylic acid (2-amino-phenyl)-amide To a solution of 15.8 mg (0.288 mmol) in 1 ml THF were added 46.7 mg (0.288 mmol) 1,1'-carbonyldiimidazol. After 1 h at rt 100 mg (0.288 mmol) {2-[(5-Aminomethyl-thiophene-2-carbonyl)-amino]-phenyl}-carbamic acid t-butyl ester were added and the reaction mixture was stirred for 1 h at rt. 1.7 ml trifluoroacetic acid were added and after 16 h at rt sat. aqueous NaHCO$_3$ was added carefully and the aqueous phase was extracted three times with ethyl acetate. The combined organic phases were dried over Na$_2$SO$_4$ and the solvent was evaporated. The residue was purified by HPLC/MS to yield 75 mg (0.228 mmol 5-[(3-Prop-2-ynyl-ureido)-methyl]-thiophene-2-carboxylic acid (2-amino-phenyl)-amide; exact MW [M+H] calc'd: 329.11; MW found [M+H]: 329.3.

EXAMPLE 6

In an analogous manner to that described in the example 5, and using known methods as described in the literature (e.g., in standard works such as Houben-Weyl, "Methoden der Organischen Chemie, Georg Thieme Verlag", Stuttgart; Organic Reactions, John Wiley & Sons, Inc., New York) the following compounds are prepared:

| Compound Name | exact MW [M + H] calc'd [g/mol] | MW found [M + H] [g/mol] |
|---|---|---|
| 6-1<br>5-[3-(2-Dimethylamino-ethyl)-ureidomethyl]-thiophene-2-carboxylic acid (2-amino-phenyl)-amide | 362.16 | 362.2 |
| 6-2<br>5-[3-(2-Diisopropylamino-ethyl)-ureidomethyl]-thiophene-2-carboxylic acid (2-amino-phenyl)-amide | 418.23 | 418.3 |
| 6-3<br>5-[3-(3-Diethylamino-propyl)-ureidomethyl]-thiophene-2-carboxylic acid (2-amino-phenyl)-amide | 404.21 | 404.3 |
| 6-4<br>5-[3-(3-Dimethylamino-2,2-dimethyl-propyl)-ureidomethyl]-thiophene-2-carboxylic acid (2-amino-phenyl)-amide<br>$^1$H-NMR (400 MHz, CD$_3$OD): δ=7.80–7.79(m, 1H), 7.31–7.25 (m, 2H), 7.18–7.07(m, 3H), 4.56(s, 2H), 3.18(s, 2H), 2.99(s, 2H), 2.94(s, 6H), 1.10(s, 6H) | 404.21 | 404.3 |
| 6-5<br>5-[3-(3-Ethoxy-propyl)-ureidomethyl]-thiophene-2-carboxylic acid (2-amino-phenyl)-amide<br>$^1$H-NMR (400 MHz, CD$_3$OD): δ=7.83–7.82(m, 1H), 7.45–7.41 (m, 4H), 7.07–7.06(m, 1H), 4.54(s, 2H), 3.54–3.48(m, 4H), 3.26–3.22(m, 2H), 1.79–1.73(m, 2H), 1.20(t, J=7.1Hz, 3H) | 377.16 | 377.3 |
| 6-6<br>5-[3-(1-Methyl-hexyl)-ureidomethyl]-thiophene-2-carboxylic acid (2-amino-phenyl)-amide | 389.2 | 389.3 |
| 6-7<br>5-(3-sec-Butyl-ureidomethyl)-thiophene-2-carboxylic acid (2-amino-phenyl)-amide | 347.15 | 347.2 |
| 6-8<br>5-[3-(2-Methyl-butyl)-ureidomethyl]-thiophene-2-carboxylic acid (2-amino-phenyl)-amide | 361.17 | 361.3 |
| 6-9<br>5-[3-(2-Acetylamino-ethyl)-ureidomethyl]-thiophene-2-carboxylic acid (2-amino-phenyl)-amide | 376.14 | 376.3 |
| 6-10<br>5-{3-[3-(2-Oxo-pyrrolidin-1-yl)-propyl]-ureidomethyl}-thiophene-2-carboxylic acid (2-amino-phenyl)-amide | 416.18 | 416.3 |
| 6-11<br>5-[3-(2-Methoxy-ethyl)-ureidomethyl]-thiophene-2-carboxylic acid (2-amino-phenyl)-amide | 349.13 | 349.3 |
| 6-12<br>5-[(3-Allyl-ureido)-methyl]-thiophene-2-carboxylic acid (2-amino-phenyl)-amide | 331.12 | 331.4 |
| 6-13<br>5-(3-Isobutyl-ureidomethyl)-thiophene-2-carboxylic acid (2-amino-phenyl)-amide<br>$^1$H-NMR (400 MHz, CD$_3$OD): δ=7.80–7.79(m, 1H), 7.36–7.21 (m, 4H), 7.06–7.05(m, 1H), 4.54(s, 2H), 2.98(d, J=6.6 Hz, 2H), 1.80–1.70(m, 1H), 0.93(d, J=6.6Hz, 6H) | 347.15 | 347.4 |
| 6-14<br>5-[3-(3-Butoxy-propyl)-ureidomethyl]-thiophene-2-carboxylic acid (2-amino-phenyl)-amide | 405.2 | 405.3 |
| 6-15<br>5-[3-(3-Dibutylamino-propyl)-ureidomethyl]-thiophene-2-carboxylic acid (2-amino-phenyl)-amide | 460.27 | 460.4 |
| 6-16<br>4-{3-[5-(2-Amino-phenylcarbamoyl)-thiophen-2-ylmethyl]-ureido}-butyric acid ethyl ester | 405.16 | 405.2 |
| 6-17<br>N-(2-Amino-phenyl)-4-[(3-pentyl-ureido)-methyl]-benzamide | 355.21 | 355.2 |
| 6-18<br>N-(2-Amino-phenyl)-4-[3-(3-diethylamino-propyl)-ureidomethyl]-benzamide | 398.26 | 398.3 |
| 6-19<br>N-(2-Amino-phenyl)-4-[3-(3-dimethylamino-2,2-dimethyl-propyl)-ureidomethyl]-benzamide<br>$^1$H-NMR (400 MHz, (CD$_3$)$_2$CO): δ=9.63(s, 1H), 7.95–7.93 (m, 2H), 7.38–7.36(m, 2H), 7.18–7.16(m, 1H), 7.00–6.96(m, 1H), 6.80–6.78(m, 1H), 6.62–6.59(m, 1H), 6.47(t, J=5.8Hz, 1H), 5.98(t, J=5.8Hz, 1H), 4.89(s, 2H), 4.30(d, J=6.1Hz, 2H), 2.94(d, J=6.1, 2H), 2.23(s, 6H), 2.07(s, 2H), 0.81(s, 6H) | 398.26 | 398.3 |
| 6-20<br>N-(2-Amino-phenyl)-4-{3-[3-(2-oxo-pyrrolidin-1-yl)-propyl]-ureidomethyl}-benzamide | 410.22 | 410.2 |

-continued

| Compound Name | exact MW [M + H] calc'd [g/mol] | MW found [M + H] [g/mol] |
|---|---|---|
| 6-21<br>4-[3-(2-Acetylamino-ethyl)-ureidomethyl]-N-(2-amino-phenyl)-benzamide | 370.19 | 370.2 |
| 6-22<br>N-(2-Amino-phenyl)-4-(3-butyl-3-methyl-ureidomethyl)-benzamide | 355.21 | 355.3 |
| 6-23<br>N-(2-Amino-phenyl)-4-[3-(2-methoxy-ethyl)-ureidomethyl]-benzamide | 343.18 | 343.2 |
| 6-24<br>N-(2-Amino-phenyl)-4-[3-(3-butoxy-propyl)-ureidomethyl]-benzamide | 399.24 | 399.3 |
| 6-25<br>N-(2-Amino-phenyl)-4-[3-(1-methyl-hexyl)-ureidomethyl]-benzamide<br>$^1$H-NMR (400 MHz, (CD$_3$)$_2$CO): δ=9.62(s, 1H), 7.94–7.92 (m, 2H), 7.37–7.35(m, 2H), 7.18–7.16(m, 1H), 7.00–6.96(m, 1H), 6.80–6.78(m, 1H), 6.62–6.59(m, 1H), 6.26(t, J=6.1Hz, 1H), 5.79(d, J=8.1Hz, 1H), 4.89(s, 2H), 4.28(d, J=6.1Hz, 2H), 3.65–3.55(m, 1H), 1.35–1.26(m, 8H), 1.02(d, J=6.6Hz, 3H), 0.87(t, J=6.8Hz, 3H) | 383.24 | 383.3 |
| 6-26<br>N-(2-Amino-phenyl)-4-[3-(3-ethoxy-propyl)-ureidomethyl]-benzamide<br>$^1$H-NMR (400 MHz, (CD$_3$)$_2$CO): δ=9.62(s, 1H), 7.94–7.92 (m, 2H), 7.37–7.35(m, 2H), 7.18–7.16(m, 1H), 7.00–6.96(m, 1H), 6.80–6.78(m, 1H), 6.62–6.59(m, 1H), 6.42(t, J=5.8Hz, 1H), 6.00(t, J=5.6Hz, 1H), 4.89(s, 2H), 4.28(d, J=6.1Hz, 2H), 3.42–3.35(m, 4H), 3.10–3.05(m, 2H), 1.65–1.58(m, 2H), 1.11(t, J=7.1Hz, 3H) | 371.21 | 371.3 |
| 6-27<br>4-[(3-Allyl-ureido)-methyl]-N-(2-amino-phenyl)-benzamide<br>$^1$H-NMR (400 MHz, (CD$_3$)$_2$CO): δ=9.63(s, 1H), 7.95–7.93 (m, 2H), 7.38–7.36(m, 2H), 7.19–7.17(m, 1H), 7.00–6.96(m, 1H), 6.80–6.78(m, 1H), 6.63–6.59(m, 1H), 6.49(t, J=6.1Hz, 1H), 6.15(t, J=5.8Hz, 1H), 5.89–5.79(m, 1H), 5.16–5.03(m, 2H), 4.90(s, 2H), 4.30(d, J=6.1Hz, 2H), 3.69–3.67(m, 2H) | 325.17 | 325.2 |
| 6-28<br>N-(2-Amino-phenyl)-4-[3-(3-isopropoxy-propyl)-ureidomethyl]-benzamide | 385.22 | 385.2 |
| 6-29<br>N-(2-Amino-phenyl)-4-(3-cyclopropylmethyl-ureidomethyl)-benzamide | 339.18 | 339.2 |
| 6-30<br>N-(2-Amino-phenyl)-4-[(3-prop-2-ynyl-ureido)-methyl]-benzamide | 323.15 | 323.2 |
| 6-31<br>4-{3-[4-(2-Amino-phenylcarbamoyl)-benzyl]-ureido}-butyric acid methyl ester | 385.19 | 385.2 |
| 6-32<br>N-(2-Amino-phenyl)-4-[3-(3-dibutylamino-propyl)-ureidomethyl]-benzamide<br>$^1$H-NMR (400 MHz, (CD$_3$)$_2$CO): δ=9.63(s, 1H), 7.94–7.92 (m, 2H), 7.37–7.35(m, 2H), 7.18–7.16(m, 1H), 7.00–6.96(m, 1H), 6.80–6.78(m, 1H), 6.63–6.59(m, 1H), 6.41(t, J=5.8Hz, 1H), 5.98(t, J=5.6Hz, 1H), 4.88(s, 2H), 4.28(d, J=5.6Hz, 2H), 3.05–3.01(m, 2H), 2.37–2.31(m, 6H), 1.53–1.46(m, 2H), 1.39–1.23(m, 8H), 0.88(t, J=7.1, 6H) | 454.32 | 454.4 |
| 6-33<br>N-(2-Amino-phenyl)-4-[3-(2-dimethylamino-ethyl)-ureidomethyl]-benzamide | 356.21 | 356.3 |
| 6-34<br>N-(2-Amino-phenyl)-4-[3-(2-diisopropylamino-ethyl)-ureidomethyl]-benzamide | 412.27 | 412.3 |
| 6-35<br>N-(2-Amino-phenyl)-4-[3-(2-methyl-butyl)-ureidomethyl]-benzamide | 355.21 | 355.3 |
| 6-36<br>N-(2-Amino-phenyl)-4-(3-isobutyl-ureidomethyl)-benzamide | 341.2 | 341.2 |
| 6-37<br>N-(2-Amino-phenyl)-4-(3-sec-butyl-ureidomethyl)-benzamide | 341.2 | 341.2 |
| 6-38<br>N-(2-Amino-phenyl)-6-[(3-pentyl-ureido)-methyl]-nicotinamide | 356.21 | 356.2 |

| Compound Name | exact MW [M + H] calc'd [g/mol] | MW found [M + H] [g/mol] |
|---|---|---|
| 6-39<br>N-(2-Amino-phenyl)-6-[3-(1-methyl-hexyl)-ureidomethyl]-nicotinamide<br>$^1$H-NMR (400 MHz, $(CD_3)_2CO$): δ=10.08(s, 1H), 9.09(s, 1H), 8.35–8.33(m, 1H), 7.46–7.44(m, 1H), 7.29–7.28(m, 1H), 7.16–7.12(m, 1H), 7.01–6.99(m, 1H), 6.90–6.87(m, 1H), 6.43 (br s, 1H), 6.02(br d, J=7.6Hz, 1H), 4.40(s, 2H), 3.61–3.59(m, 1H), 1.36–1.27(m, 8H), 1.04(d, J=6.57Hz, 3H), 0.88(t, J=6.8Hz, 3H) | 384.24 | 384.2 |
| 6-40<br>N-(2-Amino-phenyl)-6-[3-(3-butoxy-propyl)-ureidomethyl]-nicotinamide<br>$^1$H-NMR (400 MHz, $(CD_3)_2CO$): δ=9.86(s, 1H), 9.07(s, 1H), 8.32–8.29(m, 1H), 7.43–7.41(m, 1H), 7.21–7.19(m, 1H), 7.06–7.01 (m, 1H), 6.86–6.84(m, 1H), 6.70–6.66(m, 1H), 6.56–6.53 (m, 1H), 6.18(t, J=5.3Hz, 1H), 4.39(d, J=4.6Hz, 2H), 3.38 (t, J=6.3Hz, 2H), 3.36(t, J=6.3Hz, 2H), 3.11–3.06(m, 2H), 1.66–1.59(m, 2H), 1.53–1.45(m, 2H), 1.38–1.29(m, 2H), 0.89 (t, J=7.3Hz, 3H) | 400.23 | 400.2 |
| 6-41<br>N-(2-Amino-phenyl)-6-{3-[3-(2-oxo-pyrrolidin-1-yl)-propyl]-ureidomethyl}-nicotinamide | 411.21 | 411.2 |

While it is apparent that the preferred embodiments of the invention disclosed are well calculated to fulfill the objectives, benefits, and advantages of the invention, it will be appreciated that the invention is susceptible to modification, variation and change without departing from the proper scope or fair meaning of the subjoined claims.

We claim:

1. A compound of the general formula I

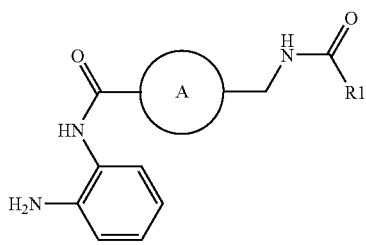

wherein
A represents phenylene;
R$^1$ represents alkyl, alkenyl, alkynyl which are all optionally substituted; or
—CH$_2$—(O—CH$_2$CH$_2$—)$_m$O-alkyl; or
—(CH$_2$)$_n$—O-alkyl; or
—(CH$_2$)$_n$—C(O)—NH-alkyl; or
—(CH$_2$)$_n$—NH—C(O)-alkyl; or
—(CH$_2$)$_n$—C(O)alkyl; or
—(CH$_2$)$_n$—C(O)—O-alkyl; or
—(CH$_2$)$_n$—O—C(O)-alkyl; or
a group —NR$^3$R$^4$, wherein R$^3$ and R$^4$ independently represent hydrogen; or
alkyl, alkenyl or alkynyl which are all optionally substituted; or
—CH$_2$—(O—CH$_2$CH$_2$—)$_m$O-alkyl; or
—(CH$_2$)$_n$—(O)-alkyl; or
—(CH$_2$)$_n$—C(O)—NH-alkyl; or
—(CH$_2$)$_n$—NH—C(O)-alkyl; or
—(CH$_2$)$_n$—C(O)-alkyl; or
—(CH$_2$)$_n$—C(O)alkyl; or
—(CH$_2$)$_n$—C(O)—O-alkyl; or
—(CH$_2$)$_n$—O—C(O)-alkyl;
n is 1–6;
m is 1–4;
or pharmaceutically acceptable salts thereof.

2. A compound according to claim 1, wherein
R$^1$ is a group —NR$^3$R$^4$, wherein R$^3$ is hydrogen;
or pharmaceutically acceptable salts thereof.

3. A compound according to claim 2, wherein
A represents 1,4-phenylene;
R$^1$ is a group —NR$^3$R$^4$, wherein
R$^3$ is hydrogen;
R$^4$ is alkenyl;
alkynyl;
—(CH$_2$)$_n$—(O)-alkyl;
—(CH$_2$)$_n$—NH—C(O)-alkyl; or
—(CH$_2$)$_n$—C(O)—O-alkyl;
n is 1–6;
or pharmaceutically acceptable salts thereof.

4. The compounds according to claim 3, wherein the compound is selected from the group consisting of:
4-[3-(2-acetylamino-ethyl)-ureidomethyl]-N-(2-amino-phenyl)-benzamide,
N-(2-amino-phenyl)-4-[3-(2-methoxy-ethyl)-ureidomethyl]-benzamide,
N-(2-amino-phenyl)-4-[3-(3-butoxy-propyl)-ureidomethyl]-benzamide,
N-(2-amino-phenyl)-4-[3-(3-ethoxy-propyl)-ureidomethyl]-benzamide,
4-[(3-allyl-ureido)-methyl]-N-(2-amino-phenyl)-benzamide,
N-(2-amino-phenyl)-4-[3-(3-isopropoxy-propyl)-ureidomethyl]-benzamide,
N-(2-amino-phenyl)-4-[(3-prop-2-ynyl-ureido)-methyl]-benzamide, and
4-{3-[4-(2-amino-phenylcarbamoyl)-benzyl]-ureido}-butyric acid methyl ester;
or pharmaceutically acceptable salts thereof.

5. A compound according to claim 2, wherein
A represents 1,4-phenylene;
R$^1$ is a group —NR$^3$R$^4$, wherein R³ is hydrogen;
R⁴ is alkyl which is unsubstituted or substituted once or several times by halogen;
—NH-alkyl; or
—N(alkyl)₂;
or pharmaceutically acceptable salts thereof.

6. The compounds according to claim 5, wherein the compound is selected from the group consisting of:
N-(2-amino-phenyl)-4-[(3-pentyl-ureido)-methyl]-benzamide,
N-(2-amino-phenyl)-4-[3-(3-diethylamino-propyl)-ureidomethyl]-benzamide,
N-(2-amino-phenyl)-4-[3-(3-dimethylamino-2,2-dimethyl-propyl)-ureidomethyl]-benzamide,
N-(2-amino-phenyl)-4-[3-(1-methyl-hexyl)-ureidomethyl]-benzamide,
N-(2-amino-phenyl)-4-[3-(3-dibutylamino-propyl)-ureidomethyl]-benzamide,
N-(2-amino-phenyl)-4-[3-(2-dimethylamino-ethyl)-ureidomethyl]-benzamide,
N-(2-amino-phenyl)-4-[3-(2-diisopropylamino-ethyl)-ureidomethyl]-benzamide,
N-(2-amino-phenyl)-4-[3-(2-methyl-butyl)-ureidomethyl]-benzamide,
N-(2-amino-phenyl)-4-(3-isobutyl-ureidomethyl)-benzamide, and
N-(2-amino-phenyl)-4-(3-sec-butyl-ureidomethyl)-benzamide,
or pharmaceutically acceptable salts thereof.

7. A compound according to claim 1, wherein
R¹ represents alkyl, alkenyl, alkynyl which are all optionally substituted; or
—CH₂—(O—CH₂CH₂)$_m$O-alkyl;
—(CH₂)$_n$—O-alkyl;
—(CH₂)$_n$—C(O)—NH-alkyl;
—(CH₂)$_n$—NH—C(O)-alkyl;
—(CH₂)$_n$—C(O)alkyl;
—(CH₂)$_n$—C(O)—O-alkyl; or
—(CH₂)$_n$—O—C(O)-alkyl;
n is 1–6;
m is 1–4;
or pharmaceutically acceptable salts thereof.

8. A compound according to claim 7, wherein
A represents 1,4-phenylene;
R¹ represents alkenyl;
—CH₂—(O—CH₂CH₂)$_m$O—CH₃;
—(CH₂)$_n$—O-alkyl; or
—(CH₂)$_n$—NH—C(O)-alkyl;
n is 1–6;
m is 1–4;
or pharmaceutically acceptable salts thereof.

9. A compound according to claim 8, selected from the group consisting of:
N-(2-amino-phenyl)-4-[(2-ethoxy-acetylamino)-methyl]-benzamide,
N-(2-amino-phenyl)-4-(pent-4-enoylamino-methyl)-benzamide,
N-(2-amino-phenyl)-4-({2-[2-(2-methoxy-ethoxy)-ethoxy]-acetylamino}-methyl)-benzamide, and
4-[(2-acetylamino-acetylamino)-methyl]-N-(2-amino-phenyl)-benzamide;
or pharmaceutically acceptable salts thereof.

10. A compound according to claim 7, wherein
A represents 1,4-phenylene;
R¹ represents alkyl; wherein the alkyl group is unsubstituted or substituted once or several times by:
halogen;
—NH-alkyl; or
—N(alkyl)₂;
or pharmaceutically acceptable salts thereof.

11. The compounds according to claim 10, wherein the compound is selected from the group consisting of:
N-(2-amino-phenyl)-4-(propionylamino-methyl)-benzamide,
N-(2-amino-phenyl)-4-(isobutyrylamino-methyl)-benzamide,
N-(2-amino-phenyl)-4-[(4-methyl-pentanoylamino)-methyl]-benzamide,
N-(2-amino-phenyl)-4-[(2-ethyl-butyrylamino)-methyl]-benzamide, and
N-(2-amino-phenyl)-4-(butyrylamino-methyl)-benzamide.
or pharmaceutically acceptable salts thereof.

12. A compound according to claim 1, wherein
R¹ represents a group —NR³R⁴, wherein R³ and R⁴ independently represent alkyl, alkenyl or alkynyl which are all optionally substituted; or
—CH₂—(O—CH₂CH₂)$_m$O-alkyl;
—(CH₂)$_n$—(O)-alkyl;
—(CH₂)$_n$—C(O)—NH-alkyl;
—(CH₂)$_n$—NH—C(O)-alkyl;
—(CH₂)$_n$—C(O)alkyl;
—(CH₂)$_n$—C(O)—O-alkyl; or
—(CH₂)$_n$—O—C(O)-alkyl;
n is 1–6;
m is 1–4;
or pharmaceutically acceptable salts thereof.

13. A compound according to claim 12, wherein
A represents 1,4-phenylene;
R¹ is a group —NR³R⁴, wherein R³ and R⁴ independently represent alkyl;
or pharmaceutically acceptable salts thereof.

14. A compound according to claim 13 wherein the compound is N-(2-amino-phenyl)-4-(3-butyl-3-methyl-ureidomethyl)-benzamide or pharmaceutically acceptable salts thereof.

15. A compound according to claim 1, wherein
A represents 1,4-phenylene;
R¹ is a group —NR³R⁴, wherein
R³ is hydrogen;
R⁴ is alkenyl;
alkynyl;
—(CH₂)$_n$—(O)-alkyl;
—(CH₂)$_n$—NH—C(O)-alkyl;or
—(CH₂)$_n$—C(O)—O-alkyl;
n is 2–6;
or pharmaceutically acceptable salts thereof.

16. A compound according to claim 1, wherein
R¹ is a group —NR³R⁴, wherein
R³ is hydrogen;
R⁴ is alkyl which is unsubstituted or substituted once or several times by halogen;
—NH-alkyl; or
—N(alkyl)₂;
or pharmaceutically acceptable salts thereof.

17. A compound according to claim 1, wherein
A represents 1,4-phenylene;
R¹ represents alkenyl;
—CH₂—(O—CH₂CH₂)$_m$O—CH₃;
—(CH₂)$_n$—O-alkyl; or
—(CH₂)$_n$—NH—C(O)-alkyl;
n is 1–6;
m is 1–4;
or pharmaceutically acceptable salts thereof.

18. A compound according to claim 1, wherein
A represents 1,4-phenylene;
$R^1$ represents alkyl; wherein the alkyl group is unsubstituted or substituted once or several times by:
halogen;
—NH-alkyl; or
—N(alkyl)$_2$;
or pharmaceutically acceptable salts thereof.

19. A compound according to claim 1, wherein
A represents 1,4-phenylene;
$R^1$ is a group —NR$^3$R$^4$, wherein $R^3$ and $R^4$ independently represent alkyl;
or pharmaceutically acceptable salts thereof.

20. A compound according to claim 1, wherein A represents 1,4-phenylene; or pharmaceutically acceptable salts thereof.

21. A compound according to claim 1, wherein $R^1$ represents alkyl, alkenyl, alkynyl which are all optionally substituted; or pharmaceutically acceptable salts thereof.

22. A compound according to claim 1, wherein $R^1$ represents
—CH$_2$—(O—CH$_2$CH$_2$)$_m$O-alkyl; or
—(CH$_2$)$_n$—O-alkyl; or
—(CH$_2$)$_n$—C(O)—NH-alkyl; or
—(CH$_2$)$_n$—NH—C(O)-alkyl; or
—(CH$_2$)$_n$—C(O)alkyl; or
—(CH$_2$)$_n$—C(O)—O-alkyl; or
—(CH$_2$)$_n$—O—C(O)-alkyl;
or pharmaceutically acceptable salts thereof.

23. A compound according to claim 1, wherein $R^1$ represents a group —NR$^3$R$^4$, wherein $R^3$ and $R^4$ independently represent hydrogen; or
alkyl, alkenyl or alkynyl which are all optionally substituted; or
—CH$_2$—(O—CH$_2$CH$_2$)$_m$O-alkyl; or
—(CH$_2$)$_n$—(O)-alkyl; or
—(CH$_2$)$_n$—C(O)—NH-alkyl; or
—(CH$_2$)$_n$—NH—C(O)-alkyl; or
—(CH$_2$)$_n$—C(O)alkyl; or
—(CH$_2$)$_n$—C(O)—O-alkyl; or
—(CH$_2$)$_n$—)—C(O)-alkyl;
n is 1–6;
m is 1–4;
or pharmaceutically acceptable salts thereof.

24. A compound of formula I-A

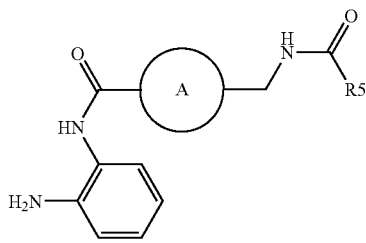

wherein
A represents 1,4-phenylene;
$R^5$ represents —(CH$_2$)$_k$-cyclopropyl;
—(CH$_2$)$_k$-cyclopentyl;
—(CH$_2$)$_k$-cyclohexyl;
—(CH$_2$)$_k$-cyclopent-2-enyl;
—(CH$_2$)$_k$-(5-oxo-pyrrolidin-2-yl);
—(CH$_2$)$_k$-(2-oxo-pyrrolidin-1-yl);
—NH—(CH$_2$)$_k$-cyclopropyl;
—NH—(CH$_2$)$_k$-cyclopentyl;
—NH—(CH$_2$)$_k$-cyclohexyl;
—NH—(CH$_2$)$_k$-cyclopent-2-enyl;
—NH—(CH$_2$)$_k$-(5-oxo-pyrrolidin-2-yl); or
—NH—(CH$_2$)$_k$-(2-oxo-pyrrolidin-1-yl);
k is 0–6;
or pharmaceutically acceptable salts thereof.

25. A compound according to claim 24, wherein the compound is selected from the group consisting of:
N-(2-amino-phenyl)-4-[(cyclopentanecarbonyl-amino)-methyl]-benzamide,
N-(2-amino-phenyl)-4-[(2-cyclopent-2-enyl-acetylamino)-methyl]-benzamide,
N-(2-amino-phenyl)-4-[(3-cyclopentyl-propionylamino)-methyl]-benzamide,
N-(2-amino-phenyl)-4-{3-[3-(2-oxo-pyrrolidin-1-yl)-propyl]-ureidomethyl}-benzamide, and
N-(2-amino-phenyl)-4-(3-cyclopropylmethyl-ureidomethyl)-benzamide;
or pharmaceutically acceptable salts thereof.

26. A process for the manufacture of a compound of formula I, said process comprising:
(a) reacting a compound of formula II

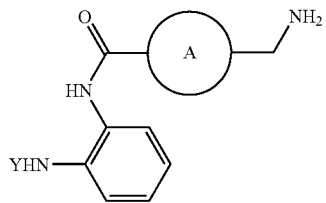

wherein A represents phenylene;
and Y represents a suitable protecting group, with a compound of the general formula III

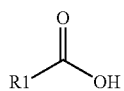

wherein
$R^1$ is alkyl, alkenyl, alkynyl which are all optionally substituted; or
—CH$_2$—(O—CH$_2$CH$_2$)$_m$O-alkyl;
—(CH$_2$)$_n$—O-alkyl;
—(CH$_2$)$_n$—C(O)—NH-alkyl;
—(CH$_2$)$_n$—NH—C(O)-alkyl;
—(CH$_2$)$_n$—C(O)alkyl;
—(CH$_2$)$_n$—C(O)—O-alkyl;
—(CH$_2$)$_n$—O—C(O)-alkyl;
and
(b) subsequent cleavage of the protection group.

27. The product of the process of claim 26.

28. The process of claim 26 further comprising the step of treating the product of the process of claim 26 with a suitable acid or base to form a pharmaceutically acceptable salt.

29. The product of the process of claim 28.

30. A process for the manufacture of a compound of formula I, said process comprising:

(a) reacting a compound of formula II

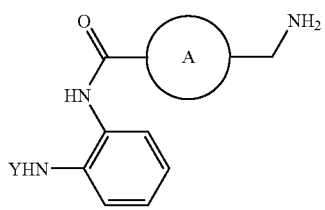

wherein A represents phenylene;
and Y represents a suitable protecting group, with a compound of the general formula X

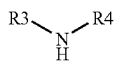

wherein $R^3$ and $R^4$ independently represent
hydrogen;
alkyl, alkenyl, alkynyl which are all optionally substituted; or
—$CH_2$—(O—$CH_2CH_2$)$_m$O-alkyl;
—$(CH_2)_n$—)-alkyl;
—$(CH_2)_n$—C(O)—NH-alkyl;
—$(CH_2)_n$—NH—C(O)-alkyl;
—$(CH_2)_n$—C(O)alkyl;
—$(CH_2)_n$—C(O)—O-alkyl;or
—$(CH_2)_n$—O—C(O)-alkyl;
n is 1–6;
m is 1–4;
and
(b) subsequent cleavage of the protection group.

31. The product of the process of claim 30.

32. The process of claim 30 further comprising the step of treating the product of the process of claim 30 with a suitable acid or base to form a pharmaceutically acceptable salt.

33. The product of the process of claim 32.

34. A pharmaceutical composition comprising a therapeutically effective amount of a compound of claim 1 and a pharmaceutically acceptable adjuvant.

35. A pharmaceutical composition comprising a therapeutically effective amount of a compound of claim 2 and a pharmaceutically acceptable adjuvant.

36. A pharmaceutical composition comprising a therapeutically effective amount of a compound of claim 7 and a pharmaceutically acceptable adjuvant.

37. A pharmaceutical composition comprising a therapeutically effective amount of a compound of claim 12 and a pharmaceutically acceptable adjuvant.

* * * * *

UNITED STATES PATENT AND TRADEMARK OFFICE
CERTIFICATE OF CORRECTION

| | | |
|---|---|---|
| PATENT NO. | : 7,098,247 B2 | Page 1 of 1 |
| APPLICATION NO. | : 10/732026 | |
| DATED | : August 29, 2006 | |
| INVENTOR(S) | : Georg Fertig et al. | |

It is certified that error appears in the above-identified patent and that said Letters Patent is hereby corrected as shown below:

Column 32, Claim 11, line 15, delete "mide." and insert
-- mide; --
Column 33, Claim 23, line 41, delete "-(CH2)n-)-C(O)-alkyl;" and insert
-- -(CH2)n-O-C(O)-alkyl; --

Signed and Sealed this

First Day of May, 2007

JON W. DUDAS
*Director of the United States Patent and Trademark Office*